United States Patent [19]
Milani

[11] Patent Number: 6,097,987
[45] Date of Patent: Aug. 1, 2000

[54] EXTERNAL DEFIBRILLATOR ELECTRODE APPARATUS

[75] Inventor: Dean Lawrence Milani, Highland Park, Ill.

[73] Assignee: Medical Research Laboratories, Inc., Buffalo Grove, Ill.

[21] Appl. No.: 09/223,605

[22] Filed: Dec. 30, 1998

[51] Int. Cl.[7] .............................. A61N 1/39; A61N 1/04
[52] U.S. Cl. ........................................ 607/142; D24/168
[58] Field of Search ..................... 607/142, 145, 607/149, 150, 115; D24/133, 144, 167, 168, 170, 187, 200

[56] References Cited

U.S. PATENT DOCUMENTS

| | | | |
|---|---|---|---|
| D. 244,153 | 4/1977 | Jones | D24/168 |
| 4,705,044 | 11/1987 | Deluhery et al. | 607/142 |
| 5,284,135 | 2/1994 | Lopin | 607/4 |

OTHER PUBLICATIONS

Two–page specification for MRL 360SLX Manual ECG Monitor/Defibrillator/Pacer, Copyright 1998.
Two–page specification for MRL 360SLX Advisory ECG Monitor/Defibrillator/Pacer, Copyright 1998.
Two–page specification for MRL Porta Pulse 3, Copyright 1998.

*Primary Examiner*—Jeffrey R. Jastrzab
*Attorney, Agent, or Firm*—Fitch, Even, Tabin & Flannery

[57] ABSTRACT

A defibrillator paddle set includes first and second paddles connected together with a Y-shaped cord set. The legs of the cord set are attached to the forward ends of each paddle, adjacent a defibrillator "firing" button. Improved manufacturing techniques and enhanced operator safety are realized.

7 Claims, 5 Drawing Sheets

EXTERNAL DEFIBRILLATOR ELECTRODE APPARATUS

BACKGROUND OF THE INVENTION

1. Field of the Invention

The present invention pertains to external defibrillators and in particular to the paddle-shaped electrodes employed therewith.

2. Description of the Related Art

Defibrillation has proven to be an effective treatment technique for alleviating certain types of cardiac malfunction, and has oftentimes been proven to be indispensable in critical life-saving situations.

Typically, an external defibrillator system includes an electronics package, a pair of defibrillator electrodes to be placed in contact with the patient's body, and one or more multi-conductor cables coupling the defibrillator electrodes and the electronics package. Typically, because the connecting cables must provide adequate high voltage electrical insulation, the cables employed are relatively bulky, heavy and inflexible. Coiling of the cables alleviates inherent stiffness to some extent, but a considerable effort must be made to manage the cables, especially during times of stress associated with life threatening situations which can be adequately addressed only by the most prompt deployment of the defibrillator equipment. With continuous coiling of the high voltage cables, extra length may be gained by uncoiling, but at times this requires a concentrated effort which must be assiduously monitored to avoid shifting careful orientation of the electrodes with respect to the patient's anatomy.

Because of the nature of the medical emergency being treated, effective monitoring of the patient's condition is oftentimes required for successful treatment. For this reason, cardiac monitoring equipment is oftentimes incorporated with the defibrillator electronics package to provide the operator with a visual indication of vital information concerning the patient's condition. When monitoring and defibrillating a patient, the optimal location of the cardiac monitoring equipment, and hence the defibrillator electronics package, is at or near the patient's head. If the cardiac monitoring equipment were placed at the feet of the patient, for example, the operator would be required to look in two opposite directions, one for addressing the medical data equipment and the other for addressing the patient's anatomy and proper orientation of the defibrillator electrodes. The optimal location allows the operator to monitor both the patient and the medical data display simultaneously, minimizing the operator's head movement and attendant change of focus.

Unfortunately, defibrillator electrodes are designed such that the interconnecting high voltage cable exits the rear of the electrode assemblies, that is, in a direction toward the patient's feet. Proper placement of the defibrillator electrodes requires the high voltage cables exiting the paddles to pass across the electrical electrodes and the hands of an operator grasping the paddles, so as to maintain their proper orientation with respect to the patient's anatomy, and to overcome distracting forces which may be applied to the cable. During this time, the operator is concerned with avoiding the passage of electrical currents to his own body as well as other people in the immediate vicinity of the medical treatment. By their nature, cardiac defibrillators are employed on an emergency basis. Whether the patient is being treated in the field or in a hospital setting, the immediate vicinity of the patient is usually very busy and considerable care must be taken to prevent unintended electrical shock of adjacent bystanders.

As mentioned above, the placement of the high voltage cables is somewhat awkward, and despite care in maintaining equipment, operators will sometimes experience micro or mild electrical shocks. During initial set-up, when first preparing for a defibrillator procedure, effective cardiac treatment time is very brief and operators are under considerable strain to effectively carry out the defibrillator procedure in an optimally efficient manner. At this critical time, an operator is required to compensate for mechanical strains and vibrations in the interconnecting high voltage cables. At times the operator is required to untangle cumbersome coiled high voltage cables, and oftentimes is required to configure the cables so as to loop over one or both hands in order to keep the high voltage cables away from the electrically active circuits of the electrodes, as previously mentioned.

Further, because the cables exit the rear of the electrodes, a longer cable length is required with the undesirable consequence that greater current leakage, greater capacitive coupling and at times compromise of the energy transfer interface results. In order to enhance energy transfer, a defibrillation gel is applied to the electrically active surface of the paddle electrodes. Because of the inherent tendency of the cables to pass across the electrically active surface of the electrodes, the cables tend to come in contact with the defibrillation gel, thus compromising their electrical insulation containing the high voltage pulse being transmitted. At a minimum, the operator's suseptance to micro shocks is heightened by the resulting contamination of the high voltage cables, with the outer surface of the cables being electrically coupled to the operator's body by the contaminating defibrillation gel.

SUMMARY OF THE INVENTION

It is an object of the present invention to provide an improved electrode apparatus for external cardiac defibrillators.

Yet another object of the present invention is to provide external defibrillator electrodes having improved cable management and reduced cable strain.

A further object of the present invention is to provide external defibrillation electrode equipment which can be employed more rapidly, and with reduced risk of injury to the operator.

These and other objects of the present invention are provided in a defibrillator paddle set, comprising:

first and second paddle bodies each having a first surface to be placed adjacent the patient's body;

an electrode carried by each body adjacent the first surface thereof;

first and second handles carried by respective paddle bodies, remote from the electrode, said handles dimensioned to wrapped about by a users fingers during operation;

a Y-shaped cord set including a junction, first and second legs extending from the junction to ones of said handles and said paddle bodies, respectively and a stem extending from said junction, away from said first and second paddle bodies;

said cord set stem including an electrical connector for connection to an external defibrillator and electrical conductors extending from said electrical connector to said junction;

said cord set first and second legs including respective electrical conductors extending from said junction to said electrodes such that said electrodes are electrically connected to said electrical connector;

the handles extending generally parallel to respective ones of said cord set first and second legs with a first end adjacent the cord set leg and a second opposed end; and electrical switch means carried by each paddle body, adjacent the cord set leg and said handle first end.

DETAILED DESCRIPTION OF THE PREFERRED EMBODIMENT

Figure 1:
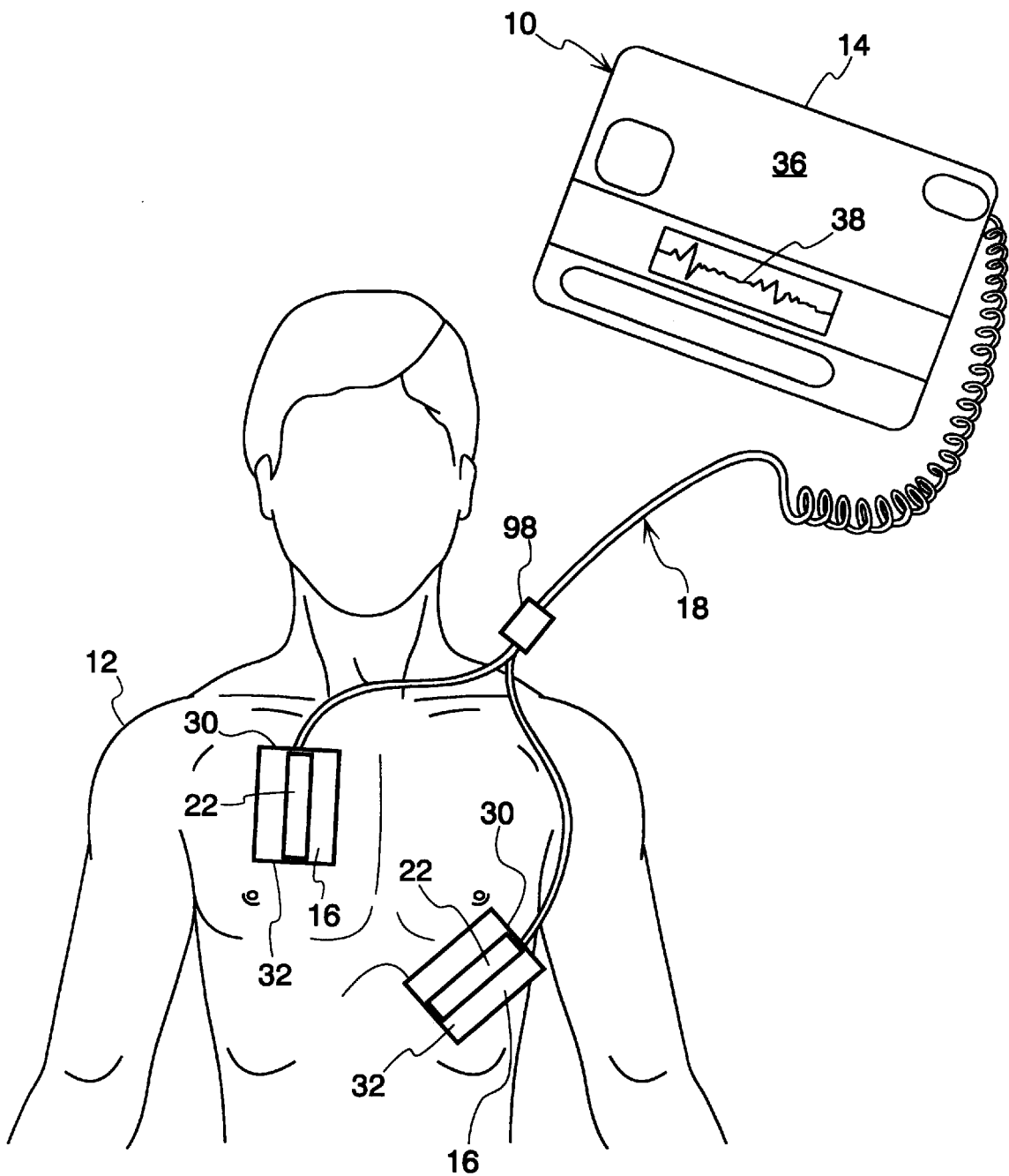
FIG. 1 shows an external defibrillator system being coupled to a patient's body in preparation for cardiac defibrillation.
Figure 2:
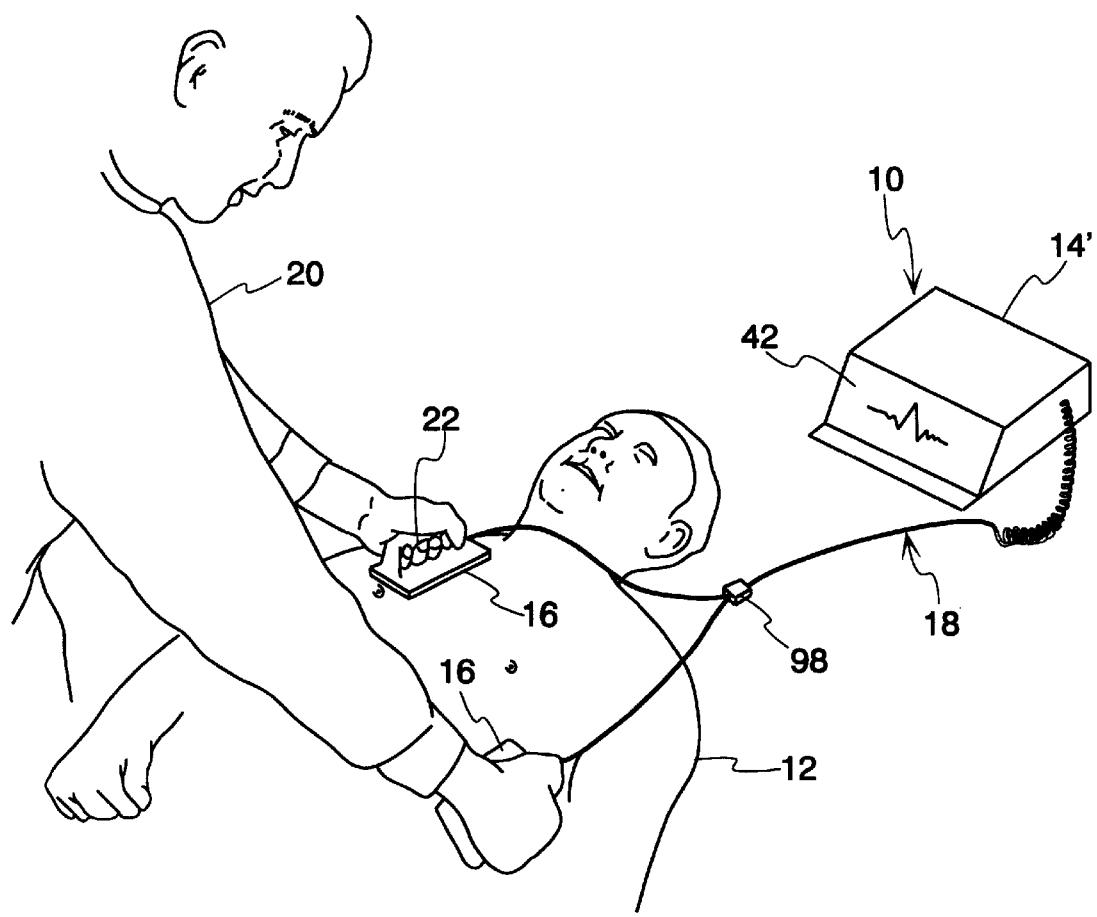
FIG. 2 is a perspective view showing an operator preparing a patient for cardiac defibrillation, using apparatus according to the principles of the present invention.

Turning now to FIGS. 1 and 2, a defibrillator system generally indicated at 10 is shown deployed, ready for cardiac defibrillation treatment of a patient 12. Defibrillator system 10 includes an electronics package 14, a pair of defibrillator electrode units or "paddles" 16 and an interconnecting high voltage cable assembly generally indicated at 18. The paddles 16 must be carefully oriented about the patient's chest area to be sure that the electrical path between the paddles, and internal to the patient's body, passes through the patient's heart so as to render effective medical relief.

With additional reference to FIG. 2, an operator 20 grasps the handles 22 of paddle 16 so as to maintain proper control of the paddles, preserving the required orientation of the paddles with respect to the patient's anatomy. Referring to FIG. 1, the paddles 16 have opposite front and rear ends 30, 32. The front ends of the paddles point generally toward the patient's head while the rear ends of the paddles point generally toward the patient's feet. As is evident from FIGS. 1 and 2, the interconnecting cables emerge from the forward ends 30 of paddles 16, lying along a direct, straight forward path between the paddle 16 and the electronics package 14.

In FIG. 1, a relatively low profile electronics package is illustrated having an upper flat surface 36 having a display window 38 for displaying medical data to the operator. In FIG. 2 a slightly different style of electronics package 14' includes a generally upstanding front face 42 with a data screen, again presenting necessary medical information to the operator, concerning the patient's condition. One example of medical information, is an electro-cardiographic presentation of the patient's cardiac functions.

It is important that the operator be able to simultaneously monitor the medical data display, the orientation of the paddles with respect to the patient's anatomy, the clearance of the equipment and the patient's body with respect to the operator's body as well as the bodies of nearby personnel. As can be seen in FIG. 2, a high voltage cable assembly 18 exits the paddle 16, in a direction away from the operator's anatomy. A high voltage cable assembly 18, in this manner, traverses the shortest distance to the electronics package 14'.

Figure 4:
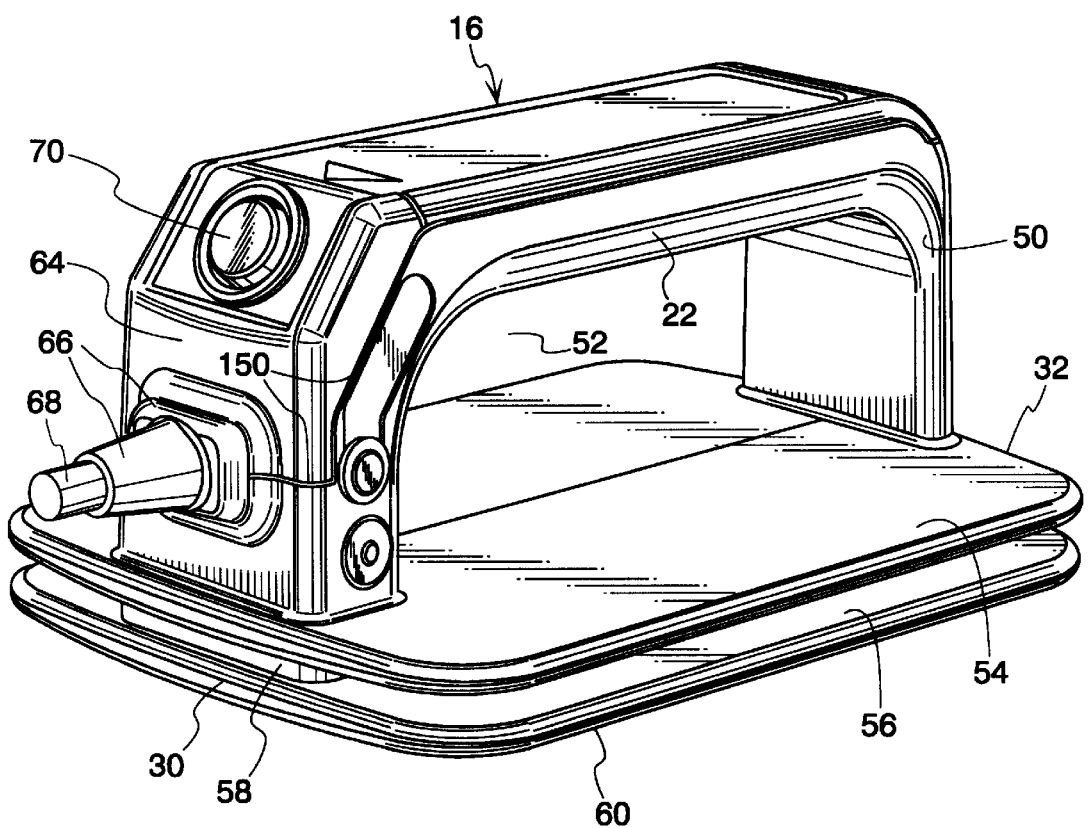
FIG. 4 is an enlarged perspective view of one of the paddles employed.

Turning now to FIG. 4, the defibrillator paddle 16 is shown in greater detail. Paddle 16 includes a structural body 50 preferably formed of molded plastic material. Handle 22 forms a closed loop with an opening 52 allowing passage of the operator's fingers, as can be seen, for example, in the upper portion of FIG. 2. Body 50 further includes first and second walls 54, 56 separated by a stand-off 58. An electrically active electrode 60 is located on the bottom surface of paddle 16. Electrode 60 is preferably made of metal plate presenting a relatively large surface area for contact with the patient's skin. It is the exposed surface of electrode 60 which receives defibrillator gel in preparation for establishing an electrically conductive path with the patient's internal tissues. The spaced-apart walls 54, 56 and the stand-off 58 provide a necessary electrical insulation to prevent creepage of high voltage electrical energy to the operator's hands, wrapped about handle 22.

The paddle 16 includes a forward wall 64 at its forward end 30. A strain relief 66 is carried on the forward wall 64, and provides mechanical support for an electrical multi-conductor cable leg 68. As can be seen in FIG. 4, electrical energy carried in cable leg 68 is directed away from the operator's hands wrapped about handle 22. Should the insulating integrity of the outer dielectric sheath of cable leg 68 of strain relief 66 be compromised as by improper handling and maintenance of the defibrillator equipment, the operator's safety and ability to effectively carry out medical treatment would be preserved.

Turning again to FIG. 4, a key-switch or electrical "firing" button 70 is carried at the forward end of paddle 16. Button 70 must be depressed in order to permit an electrical defibrillation signal to be carried along the cable assembly, and the electrically active surface of the paddles 16. As mentioned, two paddles are employed for defibrillation treatment and preferably the buttons 70 of both paddles must be simultaneously depressed before a defibrillator treatment pulse is applied to the patient.

As can be seen in FIG. 4, the "firing" button 70 is located at the forward end of the paddle 16 and provides further indication to an operator that end 30 of paddle 16 is the forward end to be directed toward the patient's head. As can be seen in FIG. 4, "firing" button 70 is located in close proximity to the cable leg 68 and, if desired, internal wiring within paddle 16 can isolate electrical high voltage at the forward end of the paddle, remote from the operator's hands, thus further contributing to operator safety and continued effectiveness of the operator's services.

Figure 3:
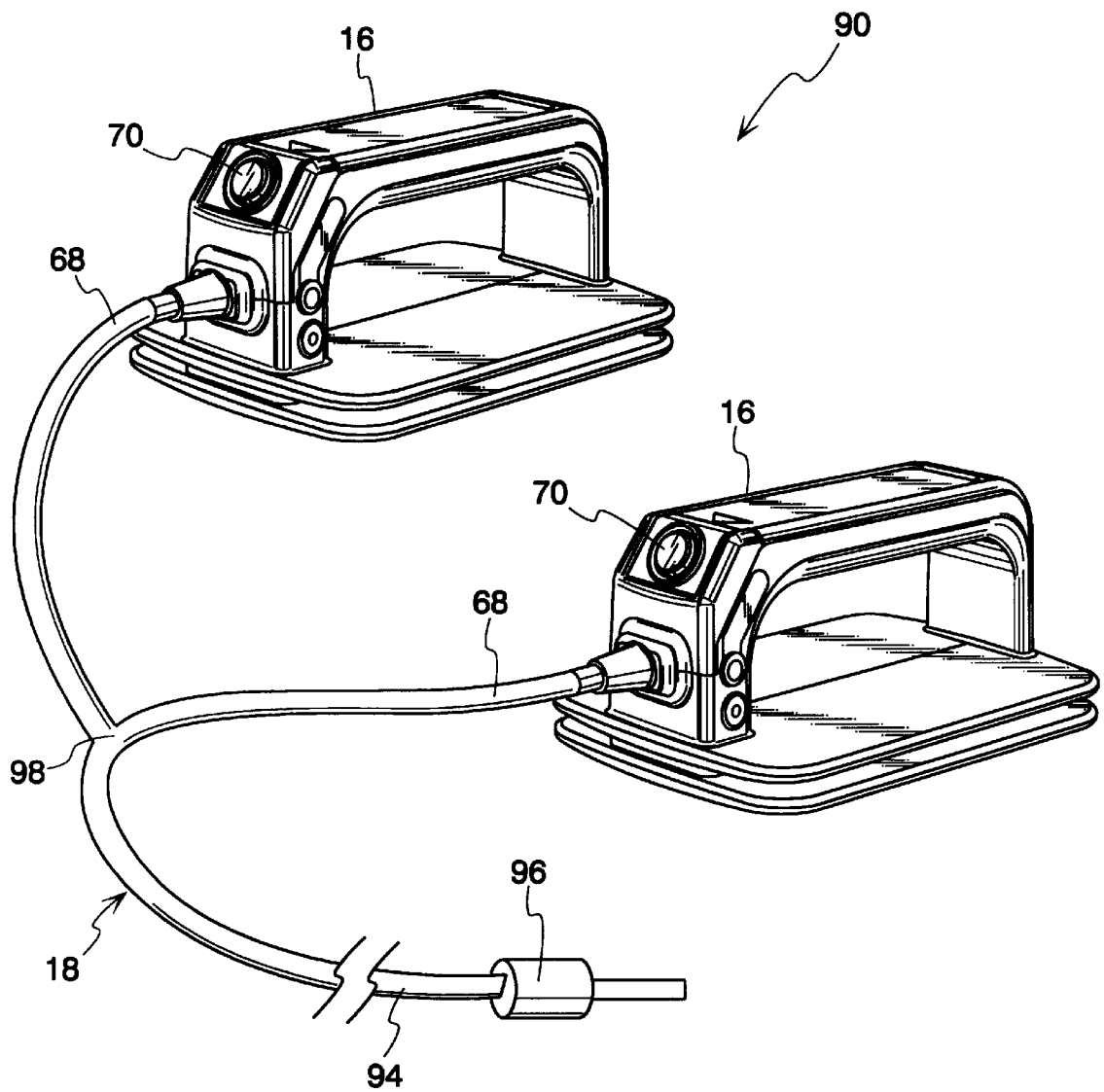
FIG. 3 shows an external defibrillator electrode or "paddle" set.

Turning now to FIG. 3, the defibrillators 16 and cable assembly 18 together comprise a defibrillator paddle set generally indicated at 90. It is preferred that the arrangement of FIG. 3 be fabricated at the factory, with the components permanently connected to one another and remaining connected to one another during their service life.

The electrical cable assembly 18 is comprised of a number of high voltage cable components, as is conventionally known. The cable assembly 18 includes individual cable legs 68 extending to each paddle 16 and a cable stem portion 94 terminated with an electrical connector 96 for electrical connection to the circuitry within the electronics package. The individual cable portions 68, 94 are preferably joined together to form a Y-shaped cord set including a junction 98, first and second legs cable legs 68, and the stem portion 94 which is coupled to the electronics package.

In the preferred embodiment, the cord set includes an outer dielectric covering, preferably of molded plastic or the like material, which defines the characteristic Y-shape. The outer covering of the Y-shaped cord set may comprise an over-molded dielectric sheath providing physical strength and integrity to the portions of the cord set (and optionally providing additional high voltage electrical insulation protection). As indicated in FIG. 3, the over-molded dielectric sheath allows a smooth continuously formed junction 98 whereas, in FIGS. 1 and 2, the junction 98 comprises an enlarged portion of dielectric material.

The junction 98 in its various forms, provides strain relief, preventing separation of the first and second legs of the cord set comprised by cables 68. As can be seen for example in FIGS. 1 and 2, the paddles 16 are spaced apart from one another during a defibrillator operation and it is important that the necessary strain relief be provided at junction 98 allowing the operator to concentrate on the medical treatment being delivered, rather than the integrity of the Y-shaped cord set.

As shown in FIGS. 1 and 2, the cable assembly 18 includes a coiled portion located adjacent the electronics package, with the remainder of the cord set having a straight, uncoiled construction. The uncoiled construction of the first and second legs of the cord set avoids entanglement of the high voltage electrical cables with the patient's clothing and it has been found easier in certain instances to train an uncoiled or straight cord set portion. With the arrangement shown in FIGS. 1 and 2, any needed strain relief or added cable length will be associated with uncoiling of the cable adjacent the more massive electronics package, further contributing to the positional stability of the cord set.

Figure 5:
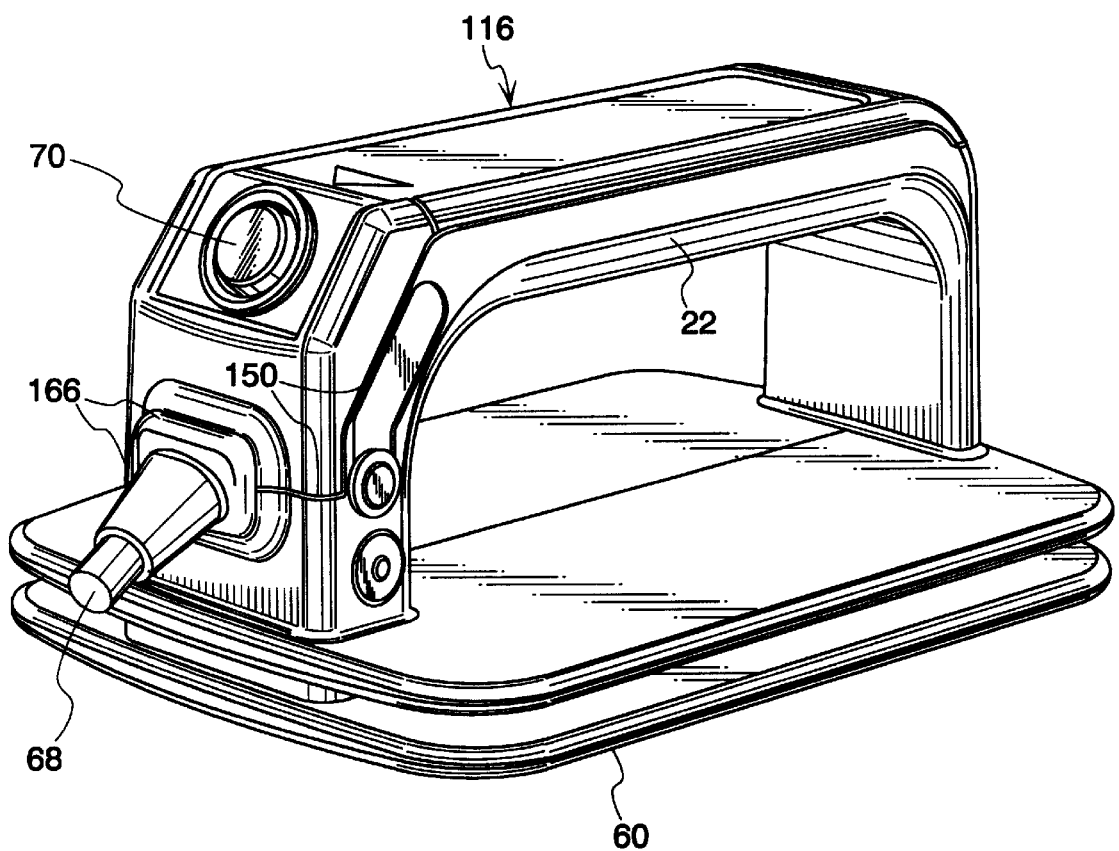
FIG. 5 is a perspective view similar to that of FIG. 4 but showing an alternative paddle illustrating other aspects of the present invention.

Turning now to FIG. 5, an alternative paddle arrangement is shown at 116. Paddle 116 is substantially identical to the paddle 16 described above except that the strain relief 166 is angled in a downward direction to further improve the physical orientation of the cord set. As can be seen for example in FIG. 2, the first and second legs of the cord set pass over the patient's body, so as to lie on the ground surface. Strain relief 166 provides directional orientation in a complementary fashion.

Certain variations are possible. For example, the strain relief 66, 166 is shown to have a relatively short dimension. If desired, the strain relief portion could be extended to have an appreciable length so as to provide greater directional control of the cord set legs. For example, as can be seen in FIGS. 1 and 2, the cord set leg of the left paddle passes over a portion of the patient's neck. It is possible that the patient may have required an emergency tracheotomy or may be receiving other treatment in the vicinity of the neck portion. It may be desirable in these instances to provide a strain relief especially adapted to the left hand paddle which would point the cord set leg away from the patient's neck region. It will be appreciated that uniquely configured strain relief members can be provided for each paddle of the defibrillator set.

As a further alternative, the strain relief members and the "firing" button can be assembled as a separate unit, being cast in electrical potting material or other dielectric medium to form a monolithic sub-assembly which is then mechanically fitted to the forward end of the paddle handle. As shown for example in FIGS. 1 and 4, a parting line 150 may be provided such that the integrally combined "firing" button 70 and strain relief 66 or 166 can be "snapped into" a paddle body. This may be useful, for example, when field modifications are urgently needed to make the best use of available equipment. For example, an operator may be called upon to render defibrillator treatment to a pediatric patient. The proper electrical energy pulse, optimized for a pediatric patient, may be incorporated into the electronics package, but it is also important that the paddle electrodes be of a size and shape for the particular patient. If a pediatric paddle set should become damaged or otherwise compromised, it may be possible to snap the paddle body with its associated electrode to the cord set of an adult defibrillator paddle unit. The integral molded "firing" button and strain relief of one cord set can be "snapped into" or releasably secured to another paddle body with the internal electrical connection to the electrode 60 being made by mating releasable electrical connectors (not shown).

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. A defibrillator paddle set, comprising:

first and second paddle bodies each having a first surface to be placed adjacent the patient's body;

an electrode carried by each body adjacent the first surface thereof;

first and second handles carried by respective paddle bodies, remote from the electrode, said handles dimensioned to wrapped about by a users fingers during operation;

a Y-shaped cord set including a junction, first and second legs extending from the junction to ones of said handles and said paddle bodies, respectively and a stem extending from said junction, away from said first and second paddle bodies;

said cord set stem including an electrical connector for connection to an external defibrillator and electrical conductors extending from said electrical connector to said junction;

said cord set first and second legs including respective electrical conductors extending from said junction to said electrodes such that said electrodes are electrically connected to said electrical connector;

the handles extending generally parallel to respective ones of said cord set first and second legs with a first end adjacent the cord set leg and a second opposed end; and electrical switch means carried by each paddle body, adjacent the cord set leg and said handle first end.

2. The defibrillator paddle set of claim 1 wherein said electrical conductors of said cord set include outer insulating coverings joined together at said junction.

3. The defibrillator paddle set of claim 1 wherein said electrical switch means carried by each paddle body are electrically coupled to the electrode carried by the paddle body.

4. The defibrillator paddle set of claim 1 wherein said handles cooperate with said paddle bodies to form a ring-shaped structure through which the operators fingers extend.

5. The defibrillator paddle set of claim 1 wherein said electrodes are flat, planar and said paddle bodies electrically insulate said handles from said electrodes.

6. The defibrillator paddle set of claim 1 wherein said cord set first and second legs extend from said paddle bodies.

7. The defibrillator paddle set of claim 1 wherein said cord set first and second legs extend from said handles.

* * * * *